US00PP23549P3

(12) United States Plant Patent
Sproul

(10) Patent No.: US PP23,549 P3
(45) Date of Patent: Apr. 23, 2013

(54) SHRUB ROSE PLANT NAMED 'SPROTHRIVE'

(50) Latin Name: *Rosa hybrida*
Varietal Denomination: Sprothrive

(75) Inventor: James A. Sproul, Bakersfield, CA (US)

(73) Assignee: CP Delaware, Inc., Wilmington, DE (US)

( * ) Notice: Subject to any disclaimer, the term of this patent is extended or adjusted under 35 U.S.C. 154(b) by 23 days.

(21) Appl. No.: 13/067,783

(22) Filed: Jun. 27, 2011

(65) Prior Publication Data

US 2012/0331594 P1 Dec. 27, 2012

(51) Int. Cl.
*A01H 5/00* (2006.01)

(52) U.S. Cl. ..... Plt./108; Plt./101; Plt./102

(58) Field of Classification Search ..... Plt./101, Plt./102, 108
See application file for complete search history.

*Primary Examiner* — Susan McCormick Ewoldt

(74) *Attorney, Agent, or Firm* — Buchanan Ingersoll & Rooney

(57) ABSTRACT

A new and distinct variety of landscape shrub rose plant is provided which forms in abundance on a substantially continuous basis attractive semi-double blossoms that are dark bright red in coloration. The vegetation is vigorous and the growth habit is round and bushy. Attractive ornamental glossy dark green foliage is formed. Superior disease resistance to blackspot is exhibited. Additionally, the new variety is particularly well suited for growing as distinctive ornamentation in the landscape.

1 Drawing Sheet

Botanical/commercial classification: *Rosa hybrida*/Shrub Rose Plant.

Varietal denomination: cv. Sprothrive.

SUMMARY OF THE INVENTION

The new variety of landscape shrub rose plant of the present invention was created by artificial pollination carried out at Bakersfield, Calif., U.S.A., wherein two parents were crossed which previously had been studied in the hope that they would contribute the desired characteristics. The female parent (i.e., the seed parent) was the product of the cross of the 'Meimonblan' variety (U.S. Plant Pat. No. 12,579) and the 'Scrivluv' variety (non-patented in the United States). The 'Scrivluv' variety sometimes is known as the 'Baby Love' variety. The male parent (i.e., the pollen parent) of the new variety was the 'Wekcisbako' variety (U.S. Plant Pat. No. 18,552). The 'Wekcisbako' male parent incorporated the 'Radrazz' variety (U.S. Plant Pat. No. 11,836) as its male parent. The parentage of the present invention can be summarized as follows:

('Meimonblan'×'Scrivluv')×'Wekcisbako'.

The seeds resulting from the above pollination were sown and small plants were obtained which were physically and biologically different from each other. Selective study resulted in the identification of a single plant of the new variety.

It was found that the new variety of landscape shrub rose plant of the present invention possesses the following combination of characteristics:

(a) abundantly and substantially continuously forms attractive semi-double blossoms that are dark bright red in coloration,
(b) exhibits a round and bushy growth habit,
(c) forms vigorous vegetation, (d) forms attractive ornamental dark green foliage with a glossy finish, and
(e) exhibits superior resistance to blackspot.

A new rose variety is provided having attractive dark bright red blooms, combined with substantially continuous blooming and blackspot resistance. The blossom coloration approaches that of fire engine red.

The new variety well meets the needs of the horticultural industry. It can be grown to advantage as attractive ornamentation in parks, gardens, public areas, and residential landscapes. Accordingly, it is particularly well suited for growing in the landscape. The dark bright red blossoms contrast nicely with the glossy green foliage.

The characteristics of the new variety have been found to be homogeneous and stable and are strictly transmissible by asexual propagation at Wasco, Calif., U.S.A., such as budding, grafting, and vegetative propagation from one generation to another. Accordingly, the new variety can be asexually reproduced in a true-to-type manner.

The new variety has been named 'Sprothrive', and will be marketed under the THRIVE! trademark.

The new variety can be readily distinguished from its ancestors upon an inspection of the blossoms. More specifically, the 'Meimonblan' variety forms marigold orange blossoms. The 'Scrivluv' variety forms deep yellow blossoms. The 'Wekcisbako' variety forms red blossoms having single petalage unlike the new variety. The 'Radrazz' variety forms blossoms of lighter red coloration. For instance, the dark bright red blossom coloration of the new variety approaches that of Red Group 46A while that of the 'Radrazz' variety commonly is between Red Group 53C and Red Group 53D of The R.H.S. Colour Chart of The Royal Horticultural Society. During observations to date, the blackspot resistance of the new variety, while superior, has been somewhat less than that of the 'Radrazz' variety.

BRIEF DESCRIPTION OF THE PHOTOGRAPH

The accompanying photograph shows, as nearly true as it is reasonably possible to make the same in a color illustration of this character, typical blossoms of the new variety. The illustrated plant was approximately three years of age and was being grown outdoors on its own roots in the field at West Grove, Pa., U.S.A.

DETAILED DESCRIPTION

The chart used in the identification of colors is that of The Royal Horticultural Society (R.H.S. Colour Chart). The description is based on the observation of three-year-old specimens of the new variety during June while grown outdoors on their own roots at West Grove, Pa., U.S.A.

Class: Landscape Shrub Rose.

Plant:

*Height*.—Approximately 4½ feet on average at the end of the growing season.

*Width*.—Approximately 3 feet on average at the end of the growing season.

*Branches/stems*.—Approximately 10 main canes per plant on average, approximately 76 cm in length on average, and approximately 1.5 cm in diameter on average.

*Habit*.—Round, and bushy.

Branches:

*Color*.—Young stems: near Yellow-Green Group 144A. Adult wood: Yellow-Green Group 144A with highlights of Greyed-Red Group 182A on areas most exposed to the sun.

*Thorns*.—Size: approximately 1 cm in length on average. Color: Greyed-Purple Group 183B.

Leaves:

*Stipules*.—Parallel with auricle facing outward, approximately 1.1 cm in length on average, and approximately 2 mm in width on average.

*Petioles*.—Upper surface: near Green Group 137B. Under surface: near Green Group 137A.

*Rachis*.—Commonly approximately 4.3 cm in length on average, and approximately 1 mm in diameter on average.

*Leaflets*.—Number: 3, 5, and 7. Shape: ovate with a serrulate margin, rounded base, and acuminate tip. Size: terminal leaflets commonly are approximately 7.5 cm in length and approximately 4.5 cm in width on average, and lower leaflets commonly are approximately 5.5 cm in length and approximately 3.5 cm in width on average. Texture: smooth. Venation: net-veined, with coloration of Yellow-Green Group 145C overlaid with Red-Purple Group 58A. Overall appearance: very dense, leathery, and dark green in coloration, with a glossy finish. Color (adult foliage): upper surface: commonly near Yellow Green Group 147A. Under surface: commonly near Yellow-Green Group 147B.

Inflorescence:

*Number of flowers*.—Commonly approximately 5 blooms per stem on average in a cluster.

*Peduncle*.—Yellow-Green Group 144A with highlights of Greyed-Red Group 182A on areas most exposed to the sun, approximately 6 cm in length on average and approximately 2 mm in diameter on average.

*Sepals*.—Number: five. Upper surface: near Yellow-Green Group 145D, somewhat soft, and tomentose. Under surface: near Yellow-Green Group 143A, somewhat rough in texture, and moderately hispidulous.

*Buds*.—Shape: ovoid. Length: approximately 2 cm on average. Diameter: commonly approximately 1.5 cm on average. Color: near Red Group 46A.

*Flower*.—Form: semi-double and informal. Diameter: approximately 5.5 cm on average. Color: upper surface: near Red Group 46A and Yellow Group 4C at the point of attachment. Under surface: near Red Group 45C and Yellow Group 4D at the point of attachment. Fragrance: none noticeable. Petal form: wedge-shaped with a curled apex. Petal length: commonly approximately 3 cm on average. Petal width: commonly approximately 3.5 cm on average. Petal margins: entire. Petal texture: glabrous on both surfaces. Petal apex: obtuse. Petal base: rounded. Petal number: approximately 10 on average. Petal drop: very good, with the petals commonly dropping cleanly and freely. Petaloids: commonly 1 to 3 per flower, broadly falcate in shape, approximately 2.5 cm in length on average, approximately 1.4 cm in width on average, and Red Group 46A in coloration with Yellow Group 4C at the point of attachment. Stamen number: approximately 10 on average. Stamen number: approximately 80 to 90 on average. Anthers: Greyed-Orange Group 163A in coloration. Filaments: Yellow-Orange Group 17B in coloration, and commonly approximately 5 to 10 mm in length. Pistils: separate and free, and commonly approximately 25 in number on average. Stigmas: Yellow-Orange Group 17C in coloration. Styles: Red Group 41B in coloration, and approximately 2 mm in length on average. Receptacle: achenes stand on the bottom and wall.

Development:

*Vegetation*.—Vigorous and strong.

*Blossoming*.—Abundant and substantially continuous.

*Resistance to diseases*.—Superior with respect to blackspot, rust and mildew.

*Propensity to form hips/seeds*.—Sparse.

*Hardiness*.—U.S.D.A. Hardiness Zone Nos. 6 to 9. The plant has thrived in a harsh Pennsylvania, U.S.A., test field for two years with no spraying or irrigation.

Plants of the new 'Sprothrive' variety have not been observed under all possible environmental conditions to date. Accordingly, it is possible that the phenotypic expression may vary somewhat with changes in light intensity and duration, cultural practices, and other environmental conditions.

I claim:

1. A new and distinct variety of landscape shrub rose plant characterized by the following combination of characteristics:

(a) abundantly and substantially continuously forms attractive semi-double blossoms that are dark bright red in coloration, (b) exhibits a round and bushy growth habit, (c) forms vigorous vegetation, (d) forms attractive ornamental dark green foliage with a glossy finish, and (e) exhibits superior resistance to blackspot;

substantially as herein shown and described.

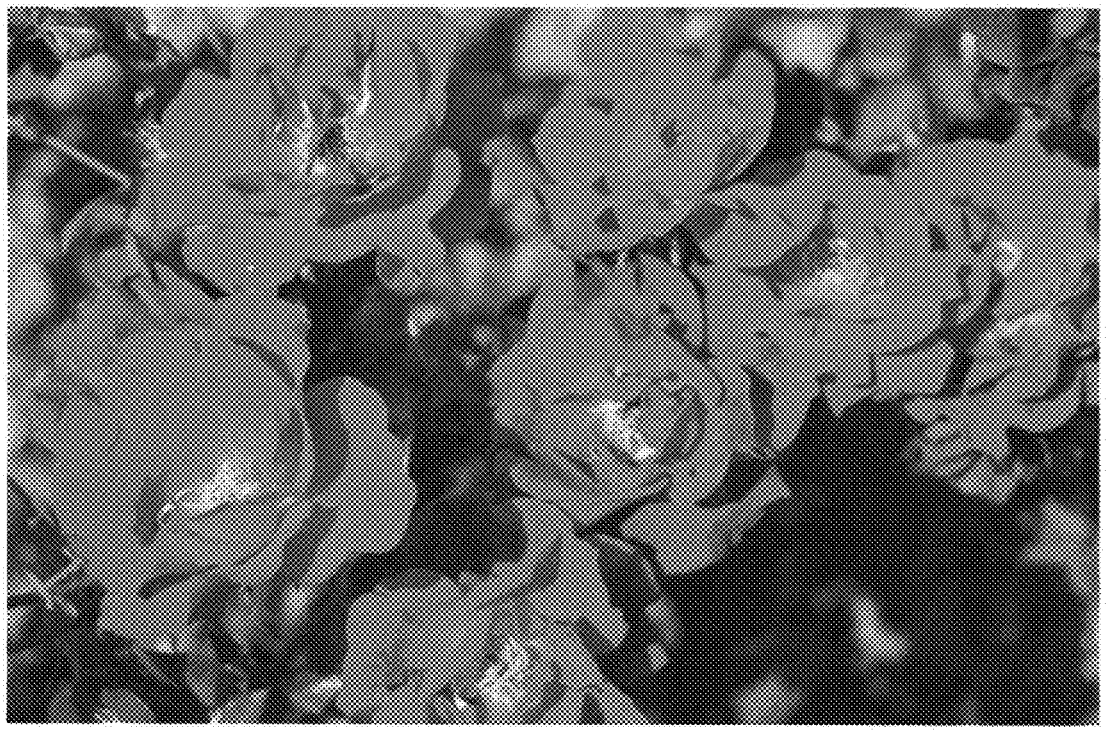

* * * * *